(12) United States Patent
Abdelkader

(10) Patent No.: US 10,603,170 B2
(45) Date of Patent: Mar. 31, 2020

(54) MEMBRANE FOR GUIDED BONE REGENERATION AND A METHOD THEREOF

(71) Applicant: Imam Abdulrahman Bin Faisal University, Dammam (SA)

(72) Inventor: Osama Abdelkader Zakaria Abdelkader, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 257 days.

(21) Appl. No.: 15/481,887

(22) Filed: Apr. 7, 2017

(65) Prior Publication Data

US 2018/0289855 A1 Oct. 11, 2018

(51) Int. Cl.
*A61F 2/28* (2006.01)
*A61L 31/12* (2006.01)
*A61L 31/14* (2006.01)

(52) U.S. Cl.
CPC .............. *A61F 2/2875* (2013.01); *A61F 2/28* (2013.01); *A61L 31/128* (2013.01); *A61L 31/14* (2013.01); *A61F 2002/2832* (2013.01); *A61F 2002/2889* (2013.01); *A61L 2400/16* (2013.01); *A61L 2430/02* (2013.01); *A61L 2430/12* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 2005/0059864 | A1 | 3/2005 | Fromovich et al. |
| 2005/0256569 | A1* | 11/2005 | Lim ...................... A61F 2/2448 623/2.36 |
| 2007/0207186 | A1 | 9/2007 | Scanlon et al. |
| 2016/0038260 | A1 | 2/2016 | Karmon |

OTHER PUBLICATIONS

Yamauchi K, et al, Self-activated mesh device using shape memory alloy for periosteal expansion osteogenesis. J Biomed Mater Res Part B, 2013:101B:736-742. (Year: 2013).*

Yamauchi K et al., "The Effect of Decortication for Periosteal Expansion Osteogenesis Using Shape Memory Alloy Mesh Device," Oct. 2015, vol. 17.

(Continued)

*Primary Examiner* — Leslie Lopez
(74) *Attorney, Agent, or Firm* — Oblon, McClelland, Maier & Neustadt, L.L.P.

(57) ABSTRACT

A membrane having at least one strip of a shape memory material and the at least one strip is sandwiched between a first layer and a second layer. A method for guiding bone regeneration which excludes the use of a tenting screw is also disclosed. The membrane may be useful for gradual displacing of the soft tissue covering bones. The gap developing between the bone and the displaced soft tissue may be filled with regenerated bone. The membrane allows the regenerated bone to form while the soft tissue heals. The membrane and method may be useful in dentistry for treating vertical bone defects. The membrane and method may also be useful for regenerating soft tissue between the bone and the displaced soft tissue.

9 Claims, 22 Drawing Sheets

(56) References Cited

OTHER PUBLICATIONS

Yamauchi K et al., "Self-Activated Mesh Device Using Shape Memory Alloy for Periosteal Expansion Osteogenesis," Jul. 2013, vol. 101, No. 5.
Ahmad Al Nashar et al., "Periosteal Distraction in Cranio-Maxillofacial Region," International Dental Journal of Student Research, Jun. 2016, vol. 4, No. 2, pp. 75-78.
Kensuke Yamauchi et al., "Self-Activated Mesh Device Using Shape Memory Alloy for Periosteal Expansion Osteogenesis," Journal of Biomedical Materials Research B: Applied Biomaterials, 2012, pp. 1-7.

* cited by examiner

MEMBRANE FOR GUIDED BONE REGENERATION AND A METHOD THEREOF

BACKGROUND

Field of the Invention

This disclosure relates to a membrane and a method for guiding tissue regeneration such as bone regeneration.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Bone augmentation requires multiple invasive procedures and costly bone grafts, scaffolds, and/or membranes. For example, alveolar ridge defects are treated by bone grafting and a membrane for guided bone regeneration, followed by soft tissue flap closure. Obtaining vertical bone height or augmenting bone in large spaces is a challenge because the soft tissue is usually sutured under tension and leads to soft tissue flap dehiscence. Complications such as premature membrane exposure and bacteria contamination may also result.

Evans et al. proposed facilitated endogenous repair as an approach to tissue engineering that avoids the ex vivo culture of autologous cells and the need for manufactured scaffolds, while minimizing the number and invasiveness of associated clinical procedures (Evans C H, Palmer G D, Pascher A, Porter R, Kwong F N, Gouze E, Gouze J N, Liu F, Steinert A, Betz O, Betz V, Vrahas M, Ghivizzani S C, Facilitated endogenous repair: making tissue engineering simple, practical, and economical, Tissue Eng. 2007 August; 13(8):1987-93, incorporated herein by reference in its entirety). This approach relies on harnessing the intrinsic regenerative potential of endogenous tissues using molecular stimuli, such as gene transfer, to initiate reparative processes in situ.

In view of the foregoing, one objective of the present disclosure is to provide a membrane and a method for guiding bone regeneration and simultaneously allowing the soft tissue to heal.

SUMMARY OF THE DISCLOSURE

The foregoing description is intended to provide a general introduction and summary of the present disclosure and is not intended to be limiting in its disclosure unless otherwise explicitly stated. The presently preferred embodiments, together with further advantages, will be best understood by reference to the following detailed description taken in conjunction with the accompanying drawings.

A first aspect of the disclosure relates to a membrane for guided bone regeneration, comprising: (i) a first layer comprising silicone and a second layer comprising silicone; and (ii) at least one strip comprising a shape memory material comprising nickel and titanium, where the at least one strip is sandwiched between the first layer and the second layer; where each of a breadth and a length of the first layer and the second layer is independently in a range of 10-60 mm, a thickness of the first layer and the second layer is independently in a range of 0.01-1 mm, a width of the at least one strip is in a range of 2-10 mm, a length of the at least one strip is in a range of 7-30 mm, a thickness of the at least one strip is in a range of 0.05-1 mm, the at least one strip is flat at a temperature in a range of 10-30° C. and is in a shape of a curve at a temperature greater than 30° C. and less than 40° C.

In one embodiment, the length of the at least one strip is in a range of 10-20 mm and the width of the at least one strip is in a range of 3-7 mm.

In one embodiment, the at least one strip is irreversibly attached to a top surface of the first layer and a bottom surface of the second layer.

In one embodiment, a mid-point of the at least one strip coincides with a mid-point of the first layer and a mid-point of the second layer.

In one embodiment, the first layer and the second layer are in a shape of a rectangle, the length is in a range of 20-30 mm, and the breadth is in a range of 10-15 mm.

In one embodiment, one strip is present and the length of the strip is disposed parallel to the length of the first layer and the second layer.

In one embodiment, each layer is in a shape of a square with the length and the breadth being the same and in a range of 20-30 mm.

In one embodiment, two strips are present, a mid-point of a first strip overlaps with a mid-point of the second strip, and the two strips are disposed perpendicularly with respect to each other.

In one embodiment, the first layer and the second layer have a same length and a same breadth.

In one embodiment, the membrane does not contain voids.

In one embodiment, the curve is an arc and a length of a chord of the arc is in a range of 40-70% of the length of the at least one strip.

In one embodiment, a length of a sagitta of the arc is in a range of 10-30% of the length of the at least one strip.

A second aspect of the disclosure relates to a method for guiding bone regeneration, comprising: (i) peeling a soft tissue flap covering a surface of a bone; (ii) inserting the membrane of the first aspect between the soft tissue flap and the surface of the bone, where a top surface of the second layer faces the soft tissue flap, a bottom surface of the first layer faces the surface of the bone; (iii) heating the at least one strip thereby expanding a space between the surface of the bone and the bottom surface of the first layer, and increasing the distance between the soft tissue flap and the surface of the bone; and (iv) leaving the membrane between the soft tissue flap and the surface of the bone thereby forming regenerated bone in the space between the surface of the bone and the bottom surface of the first layer.

In one embodiment, a height of the regenerated bone is in a range of more than 0.5 mm and up to 5 mm when the membrane is left between the soft tissue flap and the surface of the bone for a duration in a range of two to four months.

In one embodiment, the bone is located in a maxillofacial region.

In one embodiment, the bone is the alveolar ridge.

In one embodiment, the method excludes perforating the soft tissue flap with a tenting screw.

In one embodiment, the at least one strip is heated with body heat and a laser.

In one embodiment, the method further comprises: (i) harvesting the regenerated bone after the membrane is left between the soft tissue flap and the surface of the bone for at least two days; and (ii) inserting the regenerated bone into a defective bone thereby augmenting the defective bone.

In one embodiment, the method of further comprises shaping the membrane before the membrane is inserted, wherein the at least one strip is configured to outline an original bone shape when the membrane is left between the soft tissue flab and the surface of the bone.

DETAILED DESCRIPTION OF THE DISCLOSURE

Embodiments of the present disclosure will now be described more fully hereinafter with reference to the accompanying drawings, in which some, but not all embodiments of the disclosure are shown.

Within the description of this disclosure, where a numerical limit or range is stated, the endpoints are included unless stated otherwise. Also, all values and subranges within a numerical limit or range are specifically included as if explicitly written out. As used herein, the words "a" and "an" and the like carry the meaning of "one or more".

Figure 1:
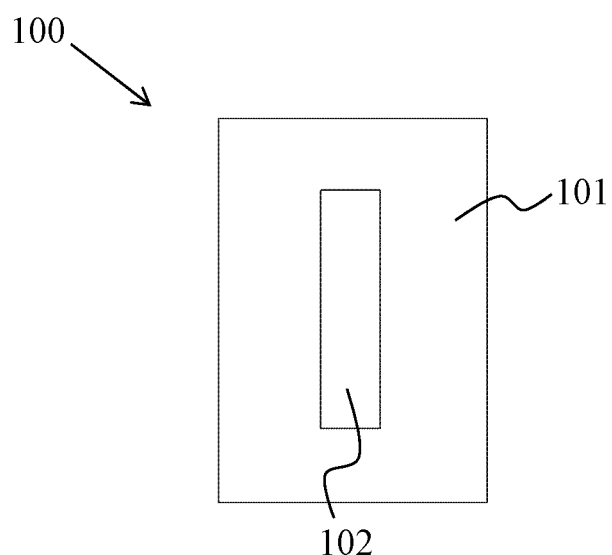
FIG. 1 shows an embodiment of the membrane with one strip.
Figure 7:
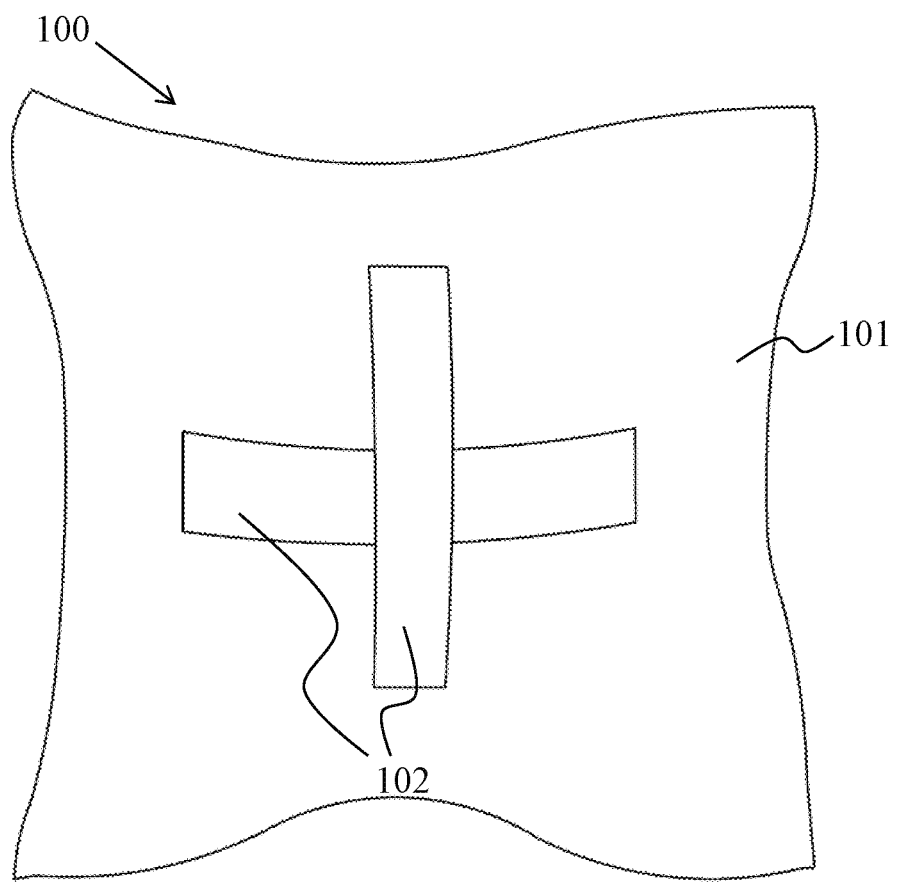
FIG. 7 shows another embodiment of the membrane which is used in Example 2.
Figure 8:
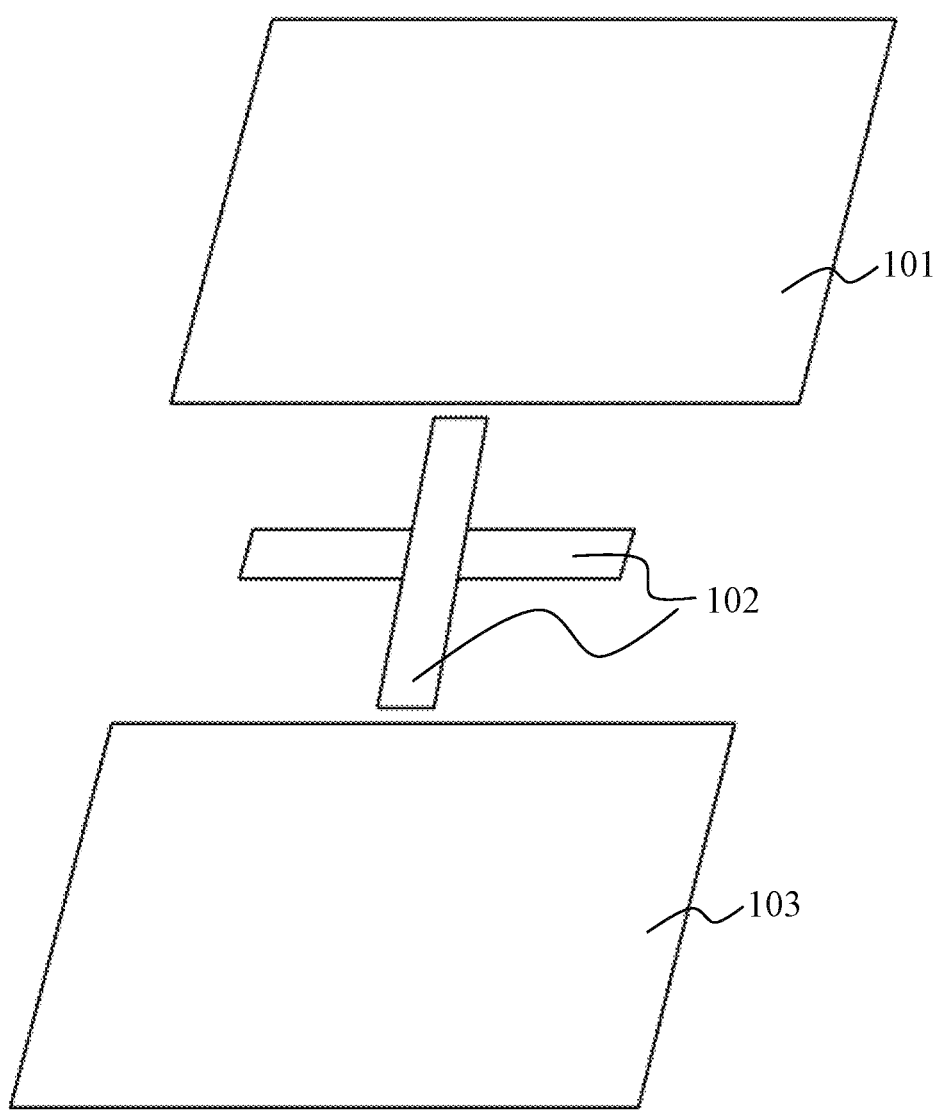
FIG. 8 shows an exploded view of the membrane in FIG. 7.

The first aspect of the disclosure relates to a membrane 100 for guided bone regeneration. The membrane 100 comprises: (i) a first layer 103 and a second layer 101, where each layer comprises silicone, and (ii) at least one strip 102 comprising a shape memory material comprising nickel and titanium, where the at least one strip 102 is sandwiched between the first layer 103 and the second layer 101. FIGS. 1, 7, and 8 show various embodiments of the membrane.

Figure 14:
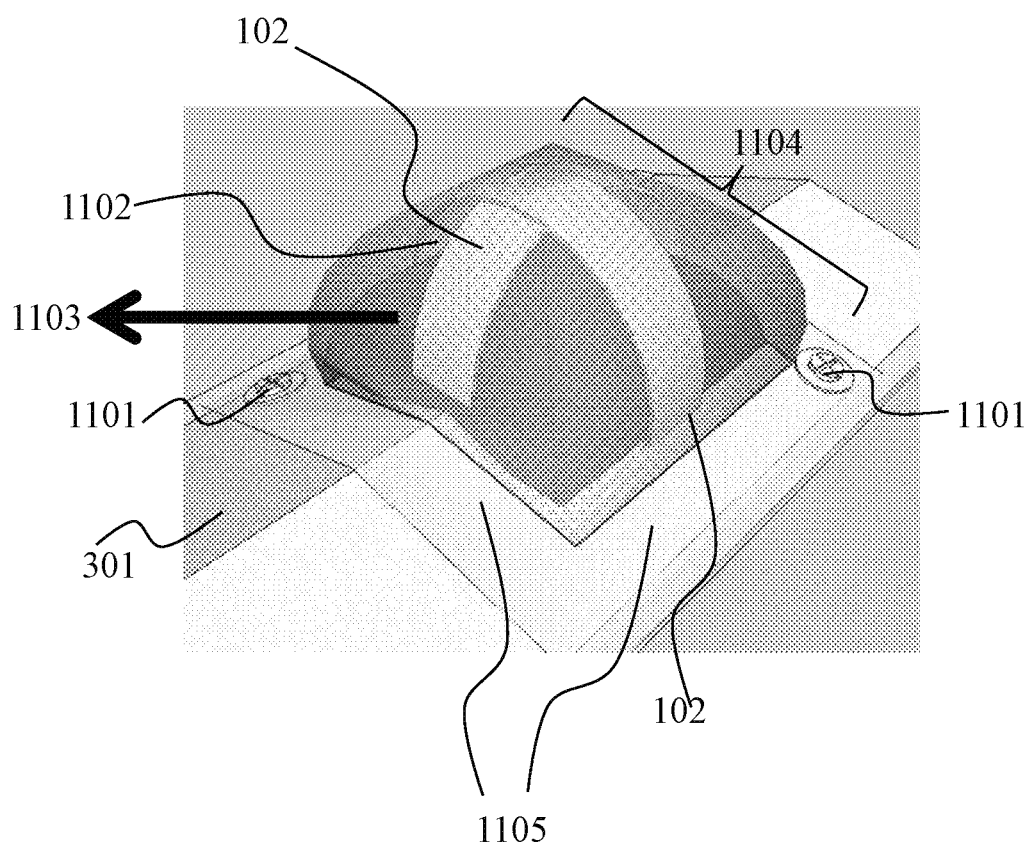
FIG. 14 shows a perspective view of a membrane on a bone after the strips are activated.

The membrane 100 has an active zone 1104 and a passive zone 1105 (FIG. 14). The active zone 1104 contains the at least one strip 102. This zone is elevated when the at least one strip 102 is activated by stimuli as described in the disclosure. The passive zone 1105 surrounds the active zone 1104. The passive zone 1105 is kept in contact with the surface of bone 301, forming a zone that the soft tissue cannot intrude.

Each of a breadth and a length of the first layer 103 and the second layer 101 is independently in a range of 10-60 mm, 10-50 mm, 10-40 mm, or 10-30 mm. Each layer may independently be in a shape of a star, a cross, a circle, an ellipse, a polygon (e.g., triangle, hexagon, rhombus, trapezium, parallelogram, pentagon, heptagon, octagon, nonagon, decagon, undecagon, and dodecagon). The polygon may be regular (i.e. all sides equal in length and all equal angles), irregular, convex (i.e. no internal angle is more than 180°), or concave. In some embodiments, each layer is in a shape of a rectangle with the length in a range of 20-40 mm, 20-35 mm, or 20-30 mm, and the breadth in a range of 10-30 mm, 10-20 mm, or 10-15 mm. In some embodiments, the breadth is 20-75%, 20-60%, 20-50%, 20-40% or 20-30% of the length. In some embodiments, each layer is in a shape of a square, and the length is in a range of 20-40 mm, 20-35 mm, or 20-30 mm.

A thickness of the first layer 103 and the second layer 101 is independently in a range of 0.01-1 mm, 0.01-0.5 mm, or 0.01-0.1 mm.

Each layer may consist of silicone. Exemplary silicones include, without limitation, dimethicone, methicone, phenyl trimethicone, and cyclomethicone. The silicone may be a medical grade silicone (e.g., at least Class VI certified). In some embodiments, each layer comprises up to 100 wt %, up to 90 wt %, up to 80 wt %, up to 70 wt %, up to 60 wt %, up to 50 wt %, up to 40 wt %, or up to 30 wt % of a carbon-based polymer, relative to the weight of silicone in the layer. In some embodiments, each layer is made entirely of a carbon-based polymer. In some embodiments, the carbon-based polymer is coated onto the surface of each layer in contact with living tissue. Exemplary carbon-based polymers include, without limitation, polyester, nylon, acacia gum, collagen (e.g., types 1-13), chitosan, polyether sulfones, fluoroelastomers (e.g., polytetrafluoroethylene (PTFE), expanded polytetrafluoroethylene (e-PTFE)), polyimides, polycarbonates, polyethylenes, polyacrylates, polyethylene glycol, biodissipative polymers (e.g., polyurethanes, polyglycolic acid (PGA), polyglactin (PGA-PLA), polycaprolactone, polydioxanone, polyglyconate (a copolymer of trimethilene carbonate and glycolide), polyorthoester, polyanhydride, polyhydroxybutyrate, poly-DL-lactic acid (DL-PLA), poly-L-lactic acid (L-PLA), and poly-D- lactic acid (D-PLA)), and combinations and/or copolymers thereof). The phrase "biodissipative material" is used herein to refer to any and all materials which dissipate without requiring surgical removal, independent of which mechanism, such as dissolution, degradation, absorption, and combinations thereof, take place. It is noted that a large number of different types of materials are known which may be inserted within the body during a surgical procedure and which later dissipate, thereby avoiding the need for a separate surgical procedure for their removal.

Biodissipative materials may start to dissipate after at least 3 months, at least 4 months, or at least 5 months, and not more than 12 months, not more than 8 months, and not more than 7 months. In another embodiment, the material may be 50% dissipated by at least 2 months, at least 3 months, or at least 9 months after insertion. In another embodiment, the material may be completely dissipated by at least 5 months, at least 6 months, or at least 10 months after insertion. The lifetime of the biodissipative material may be determined by ASTM F1635.

Each layer may comprise an additive, such as an osteoinductive material, to increase new bone formation. Exemplary osteoinductive materials include, without limitation, polymers (e.g., poly-hydroxyethylmethacrylate), proteins (e.g., bone morphogenetic protein), metals (e.g., titanium), composites (e.g., hydroxyapatite/poly(D,L-lactide), and ceramics (e.g., tricalcium phosphate, dicalcium phosphate dihydrate, dicalcium phosphate anhydrous, pyrophosphate, hydroxyapatite, biphasic calcium phosphate, carbonated apatite, octacalcium phosphate, alumina, Bioglass®, and Pyrex®). The ceramic may be derived from a coral exoskeleton or be synthetic. The synthetic ceramic may be sintered or non-sintered. Hydroxyapatite may be in a form of micron-sized particles, nanoparticles, or a mixture thereof. The additive may be present at 0.01-10 wt %, 0.1-5 wt %, or 1-3 wt %, based on a total weight of each layer.

Each layer is preferably free of hemostatic agents which may inhibit new bone formation. For example, each layer may contain less than 0.1 wt %, less than 0.05 wt %, or less than 0.01 wt % of hemostatic agents, based on a total weight of each layer. Exemplary hemostatic agents include, without limitation, aluminum potassium sulfate, aluminum sulfate, aluminum chloride, ferric sulfate, inorganic salts of organic vasoconstrictors, such as epinephrine (R or S enantiomers or racemic mixtures thereof) and pseudoephedrine, and Visine®.

Each layer may be transparent/translucent and/or transmit light. The transparency/translucency of each layer allows for the use of light-responsive shape memory materials (which are described hereinafter) in the at least one strip 102. The shape of the at least one strip 102 may change in response to ultraviolet or other types of light. Each layer is preferably transmissive to one or more of UV, visible, and IR light. In the context of the present disclosure, a material that permits at least 50%, 75%, 80%, 90% or 95% of light of any portion of the light spectrum to pass through the layer may be considered transmissive or transparent. In an alternative embodiment, each layer is colored (e.g., blue) to provide a contrast between the membrane 100 and the bone 301, thus offering better visual guidance when the surgeon attaches the membrane 100 to the bone 301. The color of each layer may be tailored by adding a dye to each layer during the manufacture of the layer. The dye may have a molecular skeleton based on anthraquinone, quinoline, acenapthene, and quinophthalone. An amount of dye may range from 1-100 ppm, preferably 30-80 ppm, more preferably 40-60 ppm, based on a total weight of each layer.

A width of the at least one strip 102 is in a range of 2-10 mm, 3-10 mm, 3-8 mm, or 3-7 mm. A length of the at least one strip 102 is in a range of 7-30 mm, 7-25 mm, 10-25 mm, or 10-20 mm. A thickness of the at least one strip 102 is in a range of 0.05-1 mm, 0.05-0.7 mm, 0.05-0.5 mm, 0.05-0.3 mm, or 0.05-0.2 mm.

The at least one strip 102 may be arranged such that a mid-point of the at least one strip 102 coincides with a mid-point of each layer. In some embodiments, the mid-point of the at least one strip 102 may be offset from the mid-point of each layer by 0.001-5 mm, 0.01-5 mm, 0.1-1 mm, or 0.1-0.5 mm, and the membrane 100 will still function as intended.

In some embodiments, the membrane 100 has one strip and the length of the strip is disposed parallel to the length of each layer. In these embodiments, each layer of the membrane 100 may be in a shape of a rectangle.

In some embodiments, the membrane 100 has two strips which are overlapped. For example, a mid-point of a first strip overlaps with a mid-point of the second strip, and the two strips are disposed perpendicularly with respect to each other.

In some embodiments, the membrane 100 has two strips or more, and each strip may have a same length and a same breadth. In other embodiments, each strip may have a different dimension from one another.

In some embodiments, the strips are arranged to form a shape of a star. Each strip may form an arm of the star. The star may have at least 5 vertices, at least 6 vertices, or at least 7 vertices, and up to 12 vertices, up to 11 vertices, or up to 10 vertices.

Figure 2:
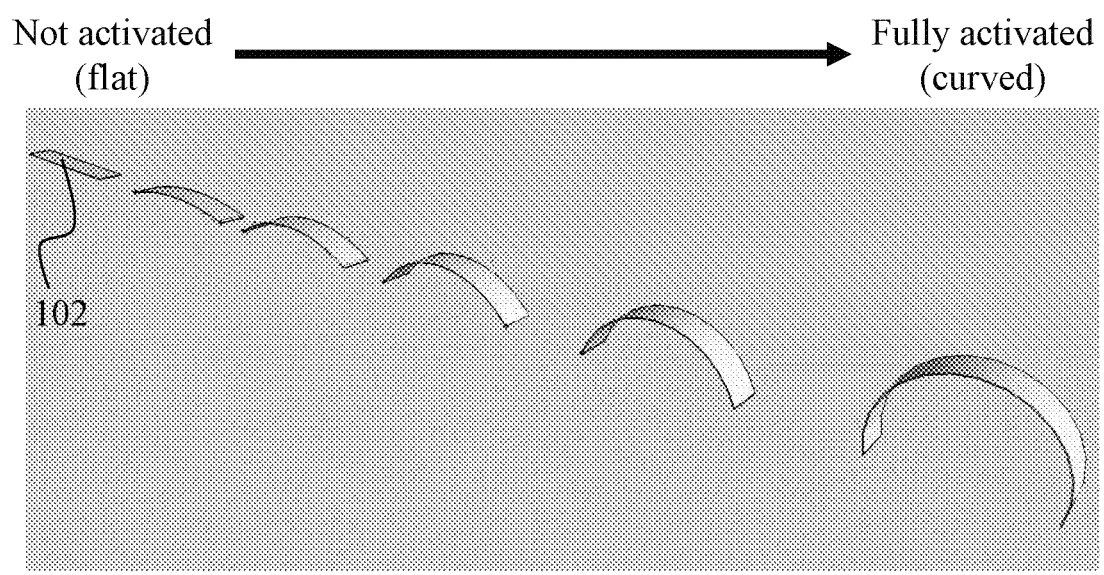
FIG. 2 shows a perspective view of the strip in FIG. 1 throughout the activation process.
Figure 9:
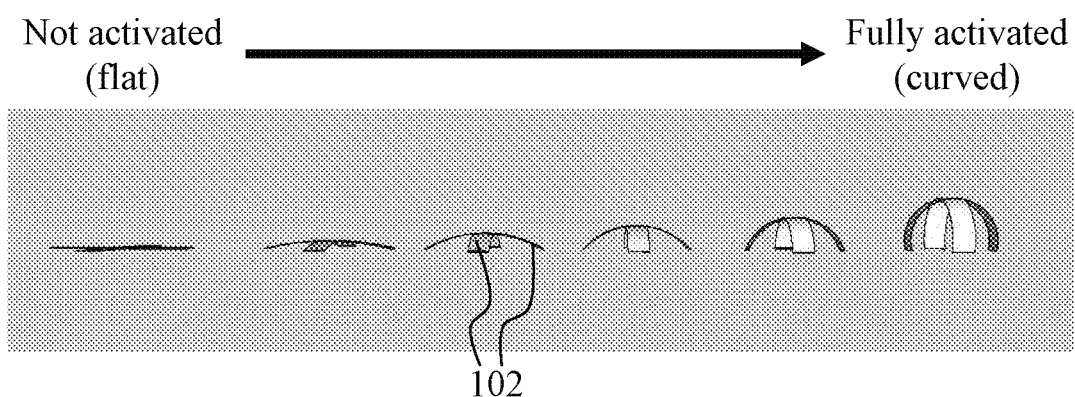
FIG. 9 shows a side view of the strips in FIG. 7 throughout the activation process.
Figure 10:
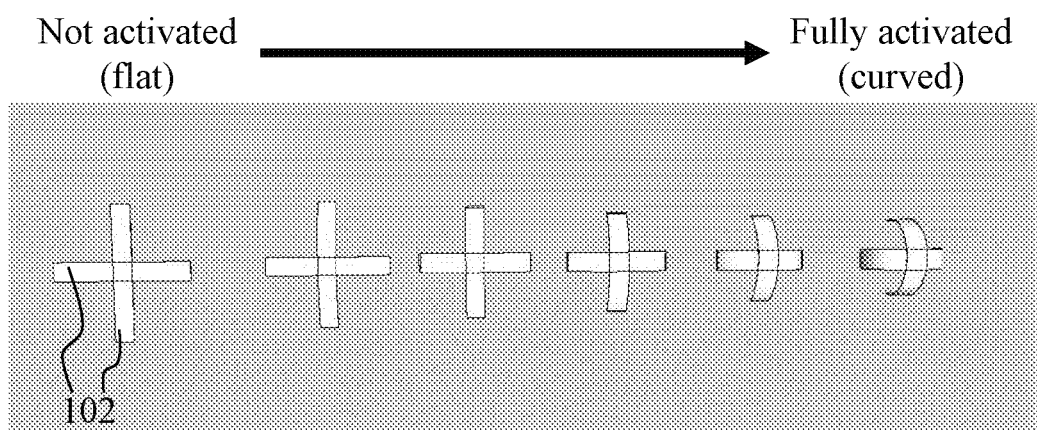
FIG. 10 shows a top view of the strips in FIG. 7 throughout the activation process.

The at least one strip 102 is flat at a temperature less than 30° C., or in a range of 0-30° C., 10-30° C., or 20-30° C. The at least one strip 102 is in a shape of a curve at a temperature greater than 30° C., greater than 31° C., greater than 32° C., greater than 33° C., greater than 34° C., greater than 35° C., greater than 36° C., and up to 42° C., up to 41° C., up to 40° C., up to 39° C., up to 38° C. The curve may be a second degree polynomial (e.g., a parabola), or a fourth degree polynomial which may be W-shaped. The curve may be in a shape of an arc (e.g., a minor arc, a major arc, or a semicircle) (FIGS. 2, 9, and 10). An angle of the minor arc may be in a range of 100-170°, 120-170°, or 140-170°. An angle of the major arc may be in a range of 190-300°, 190-270°, or 190-250°. A length of a chord of the arc, which is a straight line distance between two opposing ends of the arc, is in a range of 30-90%, 30-80%, 30-70%, or 40-70% of the length of the at least one strip 102. A length of a sagitta of the arc, which is a straight line distance between the center of the arc to the center of the chord, is in a range of 5-40%, 5-30%, or 10-30% of the length of the at least one strip 102.

The at least one strip 102 is irreversibly attached to a top surface of the first layer 103 and a bottom surface of the second layer 101. As used herein, "irreversibly attached" refers to the at least one strip 102 being intimately joined to the top surface of the first layer 103 and a bottom surface of the second layer 101 by adhesives, such as epoxy (e.g., bisphenol A epoxy, bisphenol F epoxy, glycidylamine epoxy, and novolac epoxy resin), silicone (e.g., polydimethylsiloxane and decamethyl cyclopentasiloxane), hot melt adhesives, ultraviolet light curing resins, visible light curing resins, moisture curing resins, and thermally curing resins, and cannot be detached from the layers without damaging the at least one strip 102, the layer(s), or both. In some embodiments, the adhesive may be a collagen-based adhesive (e.g., an adhesive comprising porcine collagen, poly(L- glutamic), and water-soluble carbodiimides), or a plant-based adhesive (e.g., Arabic gum, Canada balsam, latex, and starch), and combinations thereof. The aforementioned adhesives may be used to irreversibly attach the bottom surface of the second layer 101 to the top surface of the first layer 103. In some embodiments, the membrane is free of an adhesive that holds the at least one strip and layers in place. In these embodiments, the at least one strip and the layers are held together by forces such as a static force, a normal force, a surface force, and combinations thereof.

As used herein, a "shape memory material" refers to a material that remembers its original shape and can return from a deformed state to its pre-deformed shape when induced by an external stimulus (e.g., heat, light). Two important quantities that are used to describe shape memory effects are the strain recovery rate ($R_r$) and strain fixity rate ($R_f$). The strain recovery rate describes the ability of the material to memorize its permanent shape, while the strain fixity rate describes the ability of switching segments to fix the mechanical deformation. The $R_f$ and $R_r$ of the shape memory material are independently in a range of 50-100%, 60-100%, 70-100%, 80-100%, 90-100%, or 95-100%. The $R_f$ and $R_r$ may be measured by a shape memory cycle test which includes: (i) a tensile test (e.g., ASTM D638, E8, and/or F2516), and (ii) a stress-relaxation test (e.g., ASTM E328 and/or D2991) (Massad, J. E. et al., Characterization of Shape Memory Alloys for Safety Mechanisms, Sandia Report SAND2007-8000, 2008; Volk, B., Characterization of Shape Memory Polymers, each incorporated by reference in its entirety).

In embodiments where the shape memory material is activated by heat, a transformation temperature (i.e. the temperature at which the deformed material returns to its original shape) may be greater than 30° C., greater than 31° C., greater than 32° C., greater than 33° C., greater than 34° C., greater than 35° C., greater than 36° C., and up to 42° C., up to 41° C., up to 40° C., up to 39° C., or up to 38° C. The transformation temperature may be determined by ASTM F2082.

As used herein, the term "activated" refers to the transformation of the shape memory material back to its original shape. In the context of this disclosure, the shape memory material is considered to be activated when it recovered at least 10%, at least 20%, at least 30%, at least 40%, at least 50%, at least 60%, at least 70%, at least 80%, at least 90%, at least 95%, or 100% of its original shape.

The shape memory material may return to its original shape in a duration of at least 0.5 s, at least 1 s, at least 10 s, at least 60 s, at least 2 minutes, at least 10 minutes, at least 1 hour, at least 5 hours, at least 20 hours, at least 2 days, at least 4 days, at least 7 days, at least 2 weeks, or at least one month, and not more than 12 months, not more than 9 months, or not more than 6 months.

The shape memory material may be biocompatible (i.e. compatible with living tissue by not being toxic, injurious, or physiologically reactive with biochemical solids, liquids, and gases and not causing immunological response). The shape memory material may be one which is not biocompatible as the shape memory material is isolated by the layers from the bone 301 and the soft tissue.

The shape memory material may be an alloy, a polymer, or combinations thereof. The shape memory material may comprise up to 100 wt %, up to 90 wt %, up to 80 wt %, up to 70 wt %, up to 60 wt %, up to 50 wt %, up to 40 wt %, up to 30 wt %, up to 20 wt %, up to 10 wt % of a shape memory polymer, relative to a weight of the shape memory alloy. Exemplary alloys include, without limitation, nickel-titanium alloy (e.g., Nitinol and Elastinite), cobalt-chromium (e.g., Elgiloy), and nickel-cobalt (e.g., MP35N), copper-aluminum-nickel (e.g., 10-20 wt %, 10-15 wt %, or 13-15 wt % of aluminum and 1-10 wt %, 1-5 wt %, or 2-5 wt % of Ni, based on a total weight of the alloy), copper-zinc (e.g., 30-50 wt %, 35-50 wt %, or 37-42 wt % of zinc, based on a total weight of the alloy), copper-tin (e.g., 10-20 at %, 13-20 at %, or 14-16 at % of tin, based on a total amount of atoms in the alloy).

In one embodiment, the shape memory material is a nickel-titanium alloy with 50-60 wt %, 50-57 wt %, 52-57 wt %, or 55-56 wt % of nickel, based on a total weight of the alloy.

In some embodiments, the shape memory material is a polymer. Exemplary polymers, include without limitation, polyurethanes (e.g., DiAPLEX—trade name); polyethylene oxide-polyethylene terephthalate (PEO-PET) block copolymers crosslinked by at least one of maleic anhydride, glycerin, and dimethyl 5-isophthalates; polyethylene terephthalate cross-linked with at least one of maleic anhydride, glycerol, and dimethyl 5-sulfoisophthalate; polyether ether ketone; acrylic acid-methacrylic acid copolymer crosslinked with N,N'-methylene-bi s-acrylamide; methacrylic acid-N-vinyl-2-pyrrolidone copolymer crosslinked with ethyleneglycol dimethacrylate, and poly(methyl methacrylate)-N-vinyl-2-pyrrolidone copolymer crosslinked with ethyleneglycol dimethacrylate.

In some embodiments, the at least one strip 102 consists of Nitinol. In some embodiments in which there are at least two strips, each strip may be made of the same or different shape memory material. For example, one strip may be made of a shape memory alloy and at least one other strip may be made of a shape memory polymer. Further, one strip may be made of Nitinol, while at least one other strip is made of Elgiloy. In some embodiments, the at least one strip 102 and the layers are made of the aforementioned biodissipative materials therefore eliminating the need for a second surgery to retrieve the membrane 100 after regenerated bone 1103 is formed.

The shape memory material may be heated with a laser beam, body heat, an external magnetic field, and combinations thereof. The laser beam source may include any type of lasing medium which are well known by those skilled in the art. Exemplary lasing mediums include gases, such as $CO_2$, He—Ne, nitrogen, helium-copper, and neon-copper, chemical lasers, such as oxygen-iodine (COIL), all-gas-phase iodine (AGIL), hydrogen-fluoride (HF), and deuterium-fluoride (DF), excimers such as, $Ar_2^*$, $Kr_2$, $F_2^*$, $Xe_2^*$, ArF, KrF, XeBr, XeCl, XeF, and KrCl, solid state materials such as Ruby, ND:YAG, Er:YAG, Nd:YLF, Nd:YVO$_4$, Nd:YCOB, Nd:Glass, Ti:Sapphire, Tm:YAG, Yb:YAG, Yb:O$_3$, Yb:Glass, Ho:YAG, Cr:ZnSe, Ce:LiSAF, Ce:LiCAF, $^{147}Pm^{3+}$:Glass, chromium doped chroberyl, Er—Yb:Glass, Er:Glass U:CaF$_2$, Sm:CaF$_2$, and F-Center, semiconductors, such as GaN, InGaN, AlGaInP, AlGaAs, InGaAsP, VCSEL, Quantum Cascade, Hybrid Silicon, free electron lasers, photonic crystals, and dyes, such as rhodamine, fluorescein, coumarin, stilbene, umbelliferone, tetracene, and malachite green. In one embodiment, the operation wavelength of the laser is at least 700 nm and may lie in the IR region. A power of the laser may be at least 500 mW, at least 700 mW, at least 900 mW, at least 1,500 W, or at least 2,000 mW, and up to 6,000 mW, up to 5,000 mW, up to 4,000 mW, or up to 3,000 mW.

In some embodiments, the shape memory material comprises up to 50 wt %, up to 40 wt %, up to 30 wt %, up to 20 wt %, up to 10 wt %, or up to 5 wt % of magnetic particles (based on a total weight of the shape memory material) which will heat in the presence of an external magnetic field, which may be an alternating magnetic field. The magnetic particles may be made of a magnetic material which may have, or be charged with, magnetic energy. In some embodiments, the magnetic material may be a piece of a magnetically soft material that does not have polarities and can be magnetized in the presence of an external magnetic field and demagnetized in the absence of the external magnetic field. Non-limiting examples of magnetically soft materials include iron, alloys of iron and nickel, alloys of rare earth metals and commercially available materials such as Permalloy, HyMu and Mu-metal. A shape of the magnetic particle may include, but is not limited to, a cube, a cuboid, a sphere, an ellipsoid, a cylinder, and a pyramid. The magnetic particle may have a diameter at least 0.001 µm, at least 0.01 µm, at least 0.1 µm, at least 1 µm, at least 10 µm, at least 20 µm, at least 50 µm, or at least 100 µm, and up to 500 µm, up to 400 µm, up to 300 µm, or up to 200 µm. A diameter of the particle, as used herein, refers to the greatest possible distance measured from one point on the particle through the center of the particle to a point directly across from it. The frequency of the magnetic field may be in a range of 10-400 kHz, 50-300 kHz, or 100-200 kHz. An amplitude of the magnetic field may be in a range of 100-2,000 Oe, 100-1,500 Oe, or 100-1,000 Oe. A pulse duration of the magnetic field may be in a range of 1-2,000 s, 1-1,000 s, or 1-500 s. The magnetic field may be applied for a duration of 1-1,000 s, 1-500 s, or 1-200 s.

In one embodiment, the shape memory polymer is activated by light. The photo-activated shape memory polymer may transform from being flat to curved by shining light (e.g. ultraviolet light with a wavelength of 260-700 nm). The photo-activated shape memory polymer may be an acrylate-based polymer, such as polyacrylate, polymethacrylate, polyethylacrylate, polyurethane, a siloxane polymer, an epoxy polymer, an oxetane polymer or mixtures thereof. The photo-activated shape memory polymer may contain a photo-reactive pendant group which forms cross-links between adjacent photo-activated shape memory polymer chains and breaks the cross-links in response to light of different wavelengths. Exemplary photo-reactive groups include, without limitation, cinnamic, coumarin, stilbene, vinylene, chalcone, thymine, and derivatives thereof.

The membrane 100 may not contain voids. For example, the layers may be made from one continuous sheet of silicone/carbon-based polymer. The at least one strip may be made from one continuous strip of shape-memory material. In some embodiments, the membrane 100 does not contain any fluoropolymer (e.g., PTFE).

The membrane 100 is useful in a wide range of applications in which living tissue is to be expanded, stretched or displaced. The term "living tissue" is used herein to refer to any living tissue including, but not limited to, an organ, a tube, a vessel, a cavity, a bone cavity, or a membrane, and interfaces between any two or more of the above. When the membrane 100 is used within a single type of tissue, a typical application of the membrane 100 is for expanding the tissue. When the membrane 100 is used at a tissue interface, the membrane 100 is typically used to displace one of the types of tissue, in many cases for the purpose of expanding/ extending the other tissue. The membrane 100 may also be used to increase the inner dimensions of tubes, vessels, cavities, or bone cavities within the body. The membrane 100 may be used for treating horizontal bone defects, vertical bone defects, bone defects around implants, orthopedic defects, and combinations thereof.

The second aspect of the disclosure relates to a method for guiding bone regeneration. The method may depend on the gradual expansion of space above a surface of the bone for the bone to regenerate while distracting the overlying soft tissue. The method may enhance the innate potential of the body to regenerate bone without introduction of any growth factors, genes, or progenitor cells. Further, the integrity of the soft tissue may be preserved in this method. This method may decrease the need for bone grafts and lower the failure rates due to tissue dehiscence. Also, the treatment expense may be markedly reduced because the surgery for inserting the membrane is simple. When the method is applied in the field of dentistry, this method may offer an effective, expedite and economic dental therapy.

Figure 11:
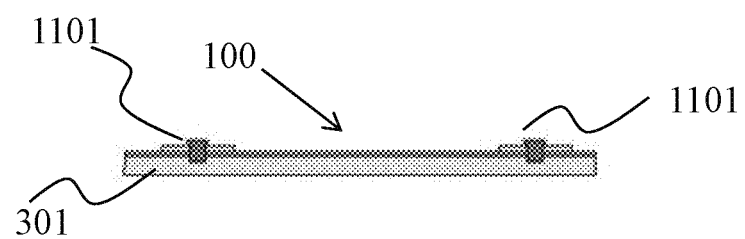
FIG. 11 shows a cross section side view of a membrane on a bone before the at least one strip is activated.

Soft tissue incisions (e.g., V-shaped or U-shaped) may be made at the site of interest (e.g., the maxillofacial region). The soft tissue may be the periosteum or the mucoperiosteum. A soft tissue elevator is inserted through the incision subperiosteally thereby elevating and peeling the soft tissue flab from the bone 301. The membrane 100 may then be inserted between the soft tissue flab and the surface of the bone 301 such that a top surface of the second layer 101 faces the soft tissue flab, and a bottom surface of the first layer 103 faces the surface of the bone 301. The membrane 100 may be attached to the surface of the bone 301 with a screw 1101, which may be made of a biocompatible metal such as stainless steel, and titanium. A screw 1101 may be placed at each corner of the membrane 100. The membrane 100 may then be covered with the soft tissue flab. FIG. 11 shows a side view of the membrane on the bone surface before the at least one strip is activated.

In some embodiments, the membrane 100 (and hence the at least one strip 102) may be irradiated with a laser to activate the at least one strip 102 before the soft tissue flab covers the membrane 100. For example, the laser described herein may irradiate the at least one strip for at least 0.1 s, at least 0.5 s, at least 1 s, at least 2 s, or at least 3 s, and up to 10 s, up to 7 s, or up to 5 s. In some embodiments, the at least one strip 102 is activated by body heat only. In some embodiments, the at least one strip 102 is activated by both laser and body heat.

Figure 12:
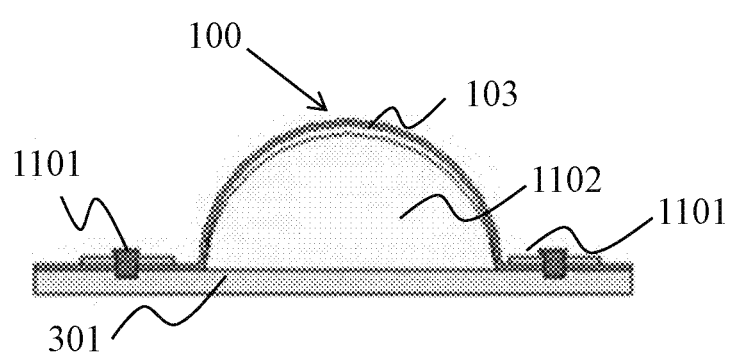
FIG. 12 shows a cross section side view of a membrane on a bone after the at least one strip is activated.
Figure 13:
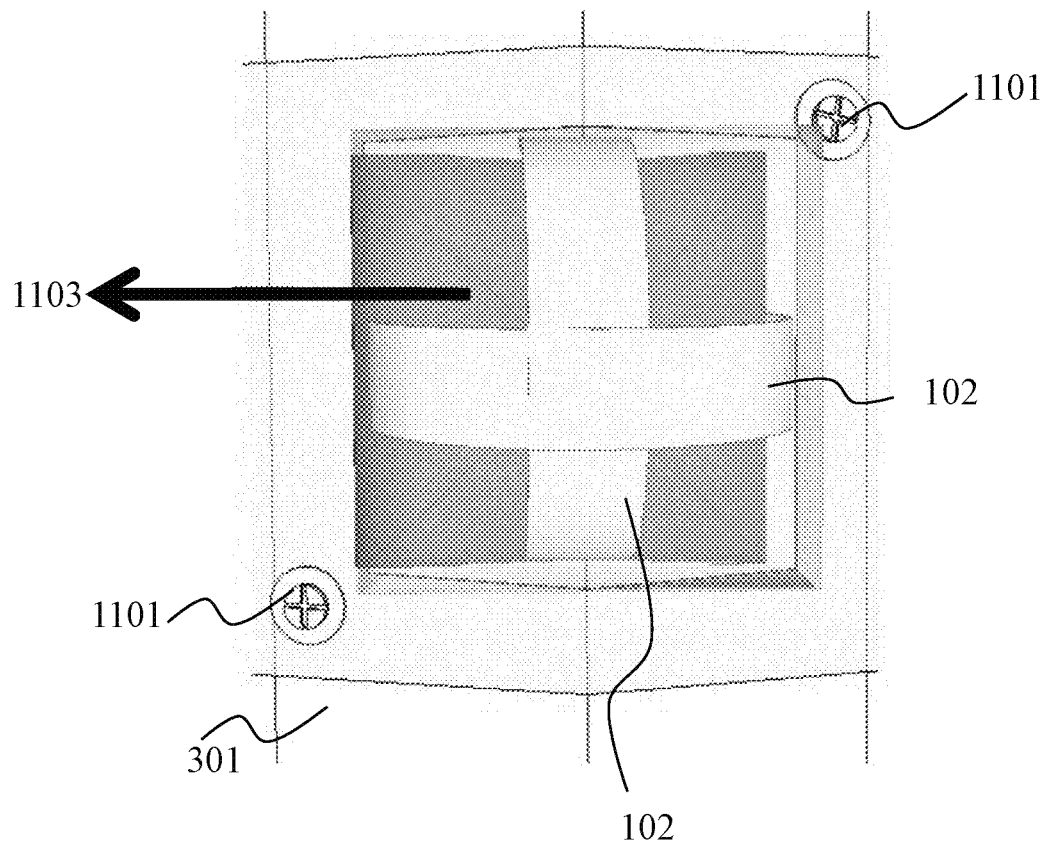
FIG. 13 shows a top view of a membrane on a bone after the strips are activated.

The distance between the soft tissue flab 305 and the surface of the bone 301 increases when the at least one strip 102 is activated thereby expanding a space 1102 between the surface of the bone 301 and the bottom surface of the first layer 103 (e.g., as shown in FIGS. 12 and 13). The space 1102 may be in a shape of a dome, a hemisphere, a square-based pyramid, a triangle-based pyramid, or a cone. A volume of the shape may be more than 50 mm$^3$, more than 100 mm$^3$, more than 150 mm$^3$, more than 250 mm$^3$, more than 300 mm$^3$, or more than 350 mm$^3$, up to 700 mm$^3$, up to 650 mm$^3$, up to 600 mm$^3$, 550 mm$^3$, or up to 500 mm$^3$. This space 1102 is expanded gradually by slowly distracting the overlying soft tissue while giving the chance for blood and growth factors from the perforated bone surface to accumulate in the expanding space 1102 thereby forming the regenerated bone 1103. The space may expand at a rate of at least 0.001 mm$^3$/s, at least 0.01 mm$^3$/s, at least 0.1 mm$^3$/s, at least 1 mm$^3$/s, at least 5 mm$^3$/s, or at least 10 mm$^3$/s, and not more than 700 mm$^3$/s, not more than 500 mm$^3$/s, not more than 300 mm$^3$/s, or not more than 100 mm$^3$/s.

The membrane 100 is left between the soft tissue flab 305 and the surface of the bone 301 thereby allowing the regenerated bone to form in the space 1102 between the surface of the bone 301 and the bottom surface of the first layer 103. Eventually, the space 1102 may be entirely/ partially filled with the regenerated bone 1103 while the overlying soft tissue heals uneventfully.

The method may exclude an exogenous stimulus such as manually turning a tenting screw to expand the space 1102 between the bone 301 and the soft tissue. Further, as the expansion of the space 1102 is achieved by activating the at least one strip 102, the disclosed method excludes perforating the soft tissue flab with a tenting screw.

A height of the regenerated bone is in a range of more than 0.5 mm, more than 1 mm, or more than 1.5 mm, and up to 5 mm, up to 4.5 mm, or up to 4 mm when the membrane 100 is left between the soft tissue flab and the surface of the bone for a duration in a range of two to four months.

In one embodiment, the bone is located in a maxillofacial region. In one embodiment, the bone is the alveolar ridge. In another embodiment, the bone is located in the calvarial region and the bone is at least one of frontal bone, parietal bone, temporal bone, occipital bone, sphenoid bone, and ethmoid bone. In one embodiment, the bone is a defective bone (i.e., a bone which lacks bone where it should normally occur). The membrane 100 may cover the cavity(s), which results from the absence of bone, and allow the regenerated bone 1103 to fill the cavity(s).

Figure 15:
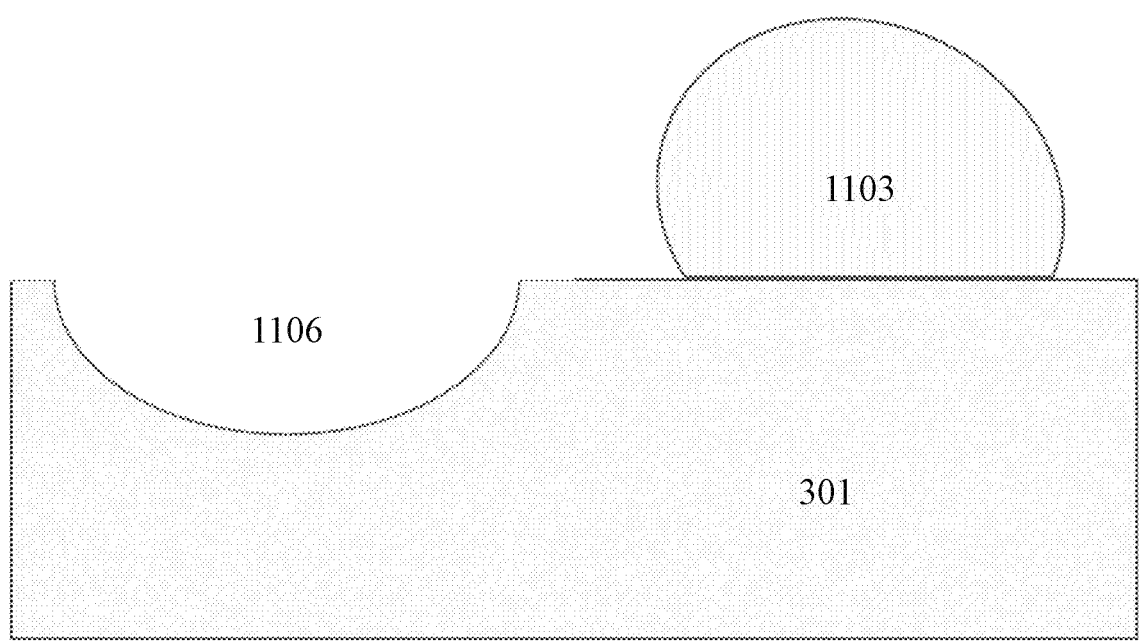
FIG. 15 is a diagram showing regenerated bone on a portion of a defective bone.

The method may be applicable in creating an in vivo bone bioreactor in humans. The in vivo bone bioreactor is a resource for harvestable engineered autogenous bone for auto grafting with little morbidity. In these embodiments, the bone is a normal (i.e., non-defective) bone. In one embodiment, the membrane 100 is attached to a non-defective portion of a defective bone (e.g., as shown in FIG. 15). In these embodiments, the regenerated bone 1103 may be surgically harvested after removing the membrane 100. The regenerated bone may be harvested after the membrane has been left in the body for at least 1 month, at least 2 months, at least 4 months, or at least 6 months, and up to 24 months, up to 18 months, up to 15 months, up to 12 months, up to 10 months, or up to 8 months. The harvested bone may then be inserted into a bone cavity 1106 thereby augmenting the defective bone. The methods of bone grafting (i.e., harvesting the regenerated bone and inserting the harvesting bone into the bone cavity) are known to those of ordinary skill in the art. This procedure may be useful when the cavity is large (e.g., more than 1,500 mm$^3$, more than 2,000 mm$^3$, or more than 2,500 mm$^3$, and up to 4,000 mm$^3$, up to 3,500 mm$^3$, or up to 3,000 mm$^3$).

The method may also be useful for forming regenerated bone with the original or a desired shape and/or restoring the original shape and size of the resorbed bone (e.g., restoring the dimensions of resorbed alveolar ridge resulting from an absence of teeth for long periods, and restoring the dimensions of bone defects in maxillofacial region resulting from trauma or pathology).

In these embodiments, the defective bone may be scanned with, for example, a computed tomograph (CT) and/or a magnetic resonance imaging (MRI) scanner. In some embodiments, the original bone may be scanned before the defects are present. The scanned data may be fed to, for example, a computer-aided design (CAD) software, for generating a digital three-dimensional image reflecting the bone defect(s). An outline of the desired or the original shape of the bone may be drawn with the same CAD software. This outline may be sent to a 3D printer which prints the at least one strip 102 with the aforementioned shape memory materials into the shape of the outline. The at least one strip 102 may then be deformed into a flat strip which may be easier to handle in the process of making the membrane 100. The deformation may occur by, for example, cooling the at least one strip 102 below the transformation temperature.

Figure 3:
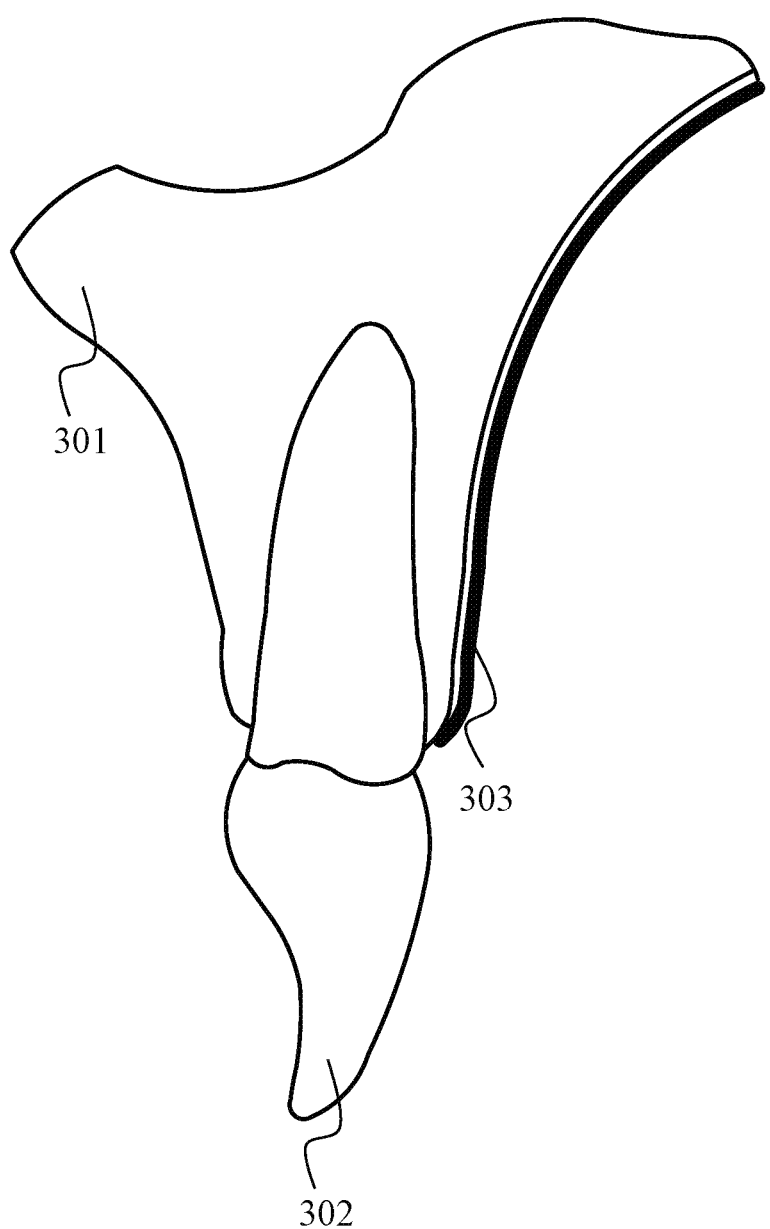
FIG. 3 shows a lateral view of a region in the mouth with a soft tissue defect.
Figure 4:
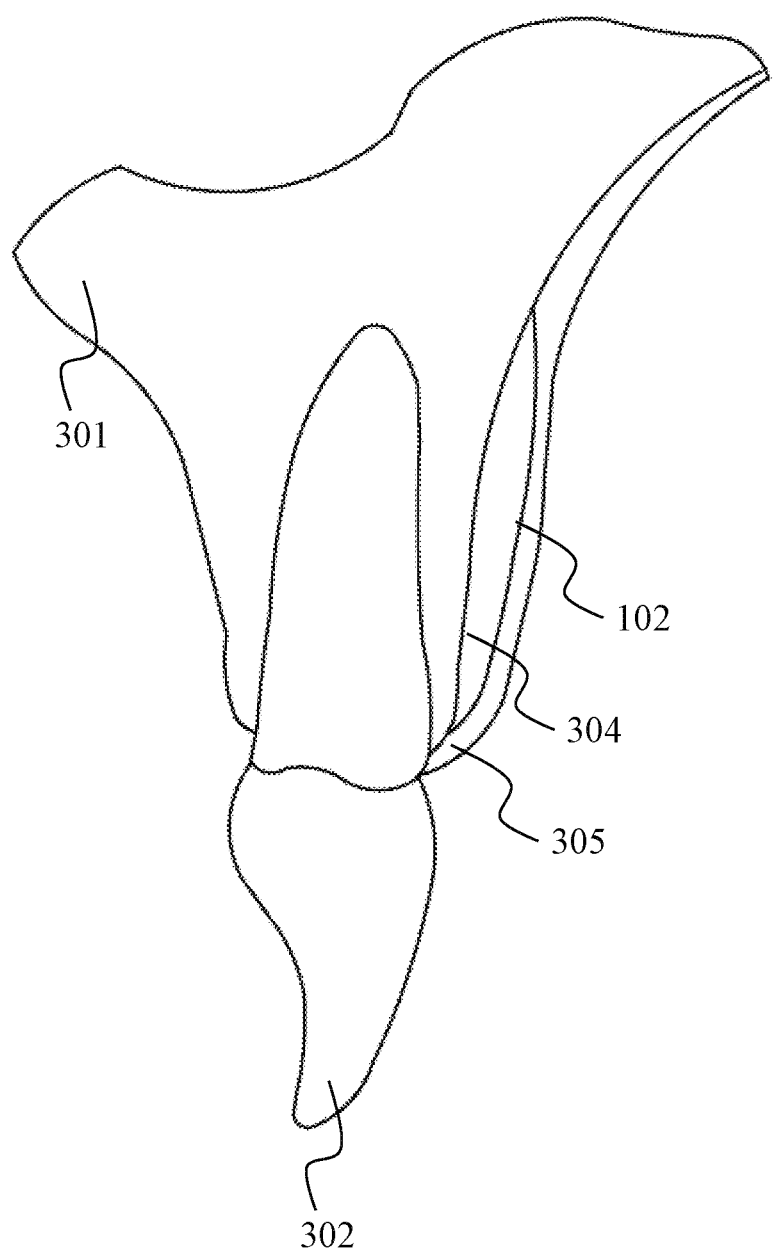
FIG. 4 shows a lateral view of the region in FIG. 3 after the strip is inserted.
Figure 5:
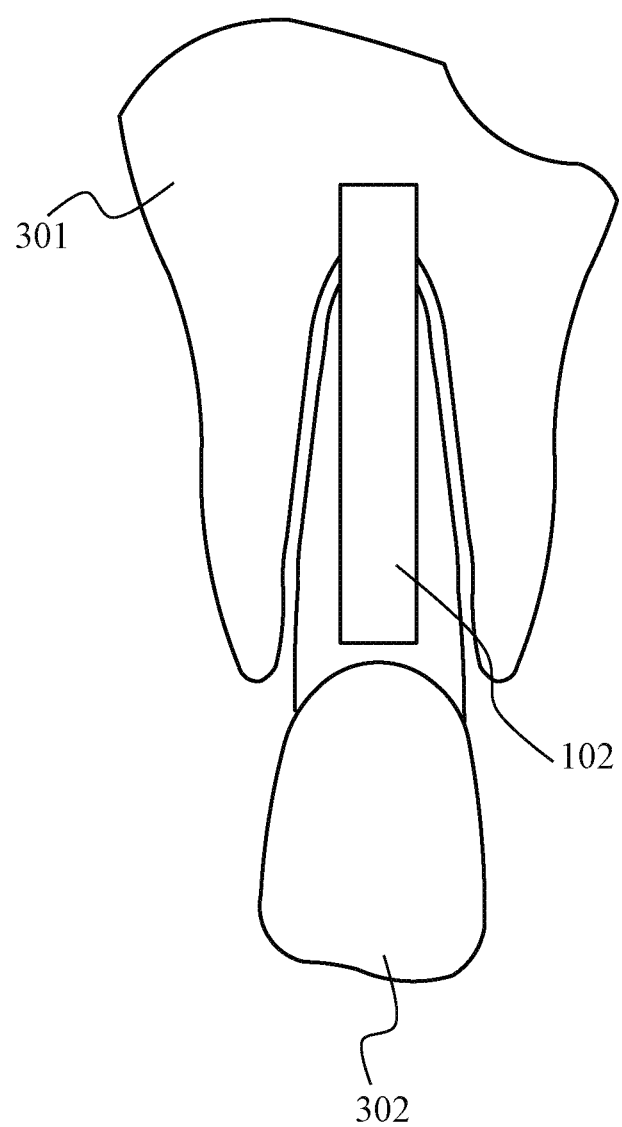
FIG. 5 shows a labial view of FIG. 4.
Figure 6:
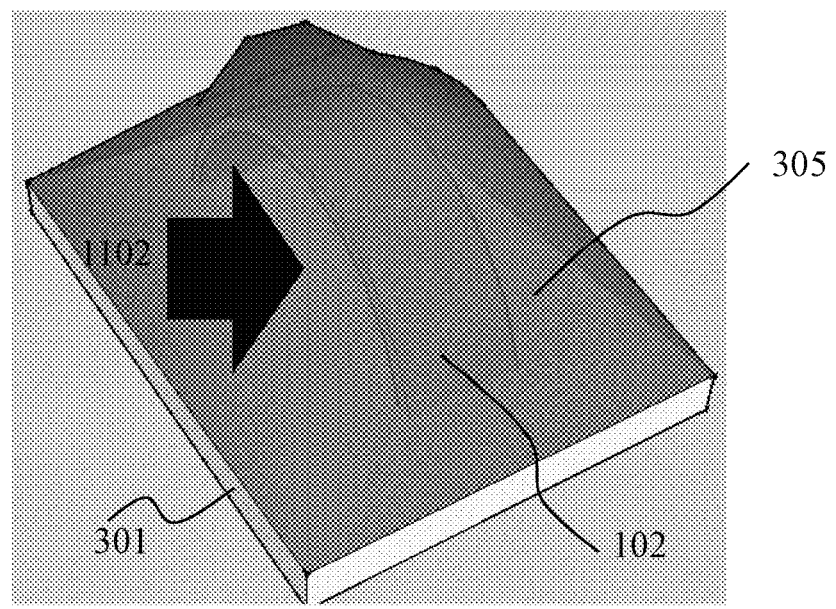
FIG. 6 shows an expanded perspective view of FIG. 4.

In one embodiment, the membrane is used for guiding soft tissue regeneration (e.g., as shown in FIGS. 4-6). In this embodiment, the membrane comprises of one strip 102 which is wrapped with a material comprising silicone to isolate the strip from direct contact with the body tissue. Further, the membrane is in a shape of the strip and may be referred to as the "strip". A soft tissue defect 303 (e.g., as shown by a bold line in FIG. 3) causes aesthetic problems, regardless whether a bone defect is present. The soft tissue defect may appear as a collapsed/recessed region and may occur at the site of extracted tooth or for a tooth 302 adjacent to the extracted tooth. The strip may be placed under a mucoperiosteal flab to tent the overlying soft tissue 305 and allow new soft tissue 304 to grow in the space 1102.

Example 1 Determining a Length of the at Least One Strip

Figure 16:
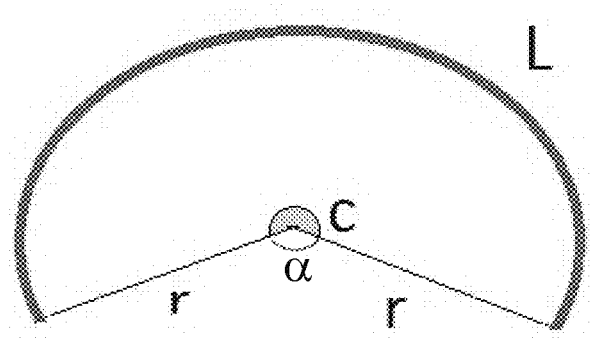
FIG. 16 shows a side view of the arc formed after strip is activated.
Figure 17:
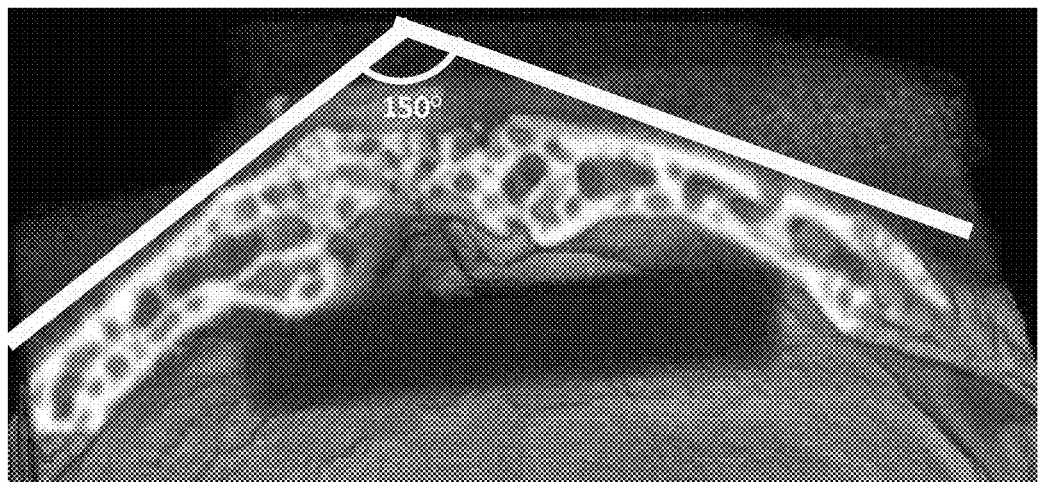
FIG. 17 is a micro computed tomography (micro CT) image of the calvarial of a rabbit.
Figure 18A:
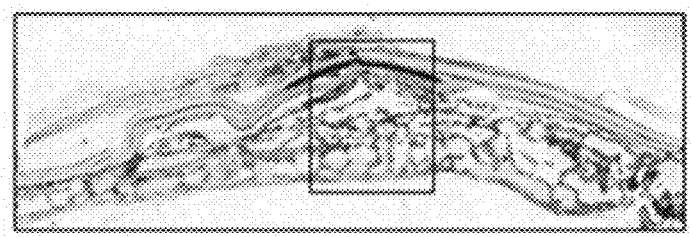
FIG. 18A is a histological image of the calvarial of the rabbit in the experimental group in which the membrane was left in the rabbit for 4 months.
Figure 18B:
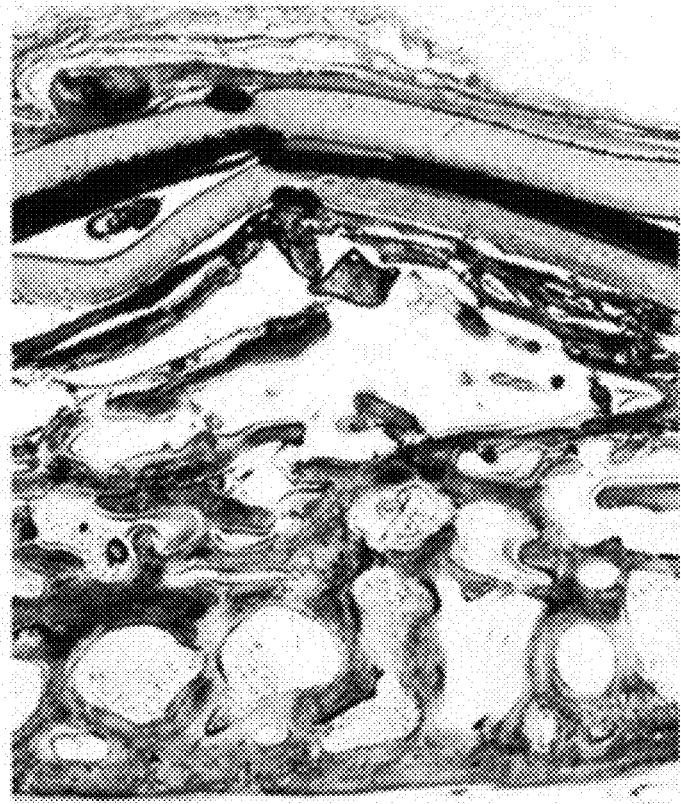
FIG. 18B shows an expanded view of the boxed region in FIG. 18A.
Figure 19A:
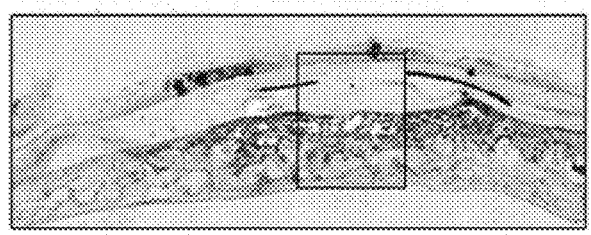
FIG. 19A is a histological image of the calvarial of the rabbit in the experimental group in which the membrane was left in the rabbit for 2 months.
Figure 19B:
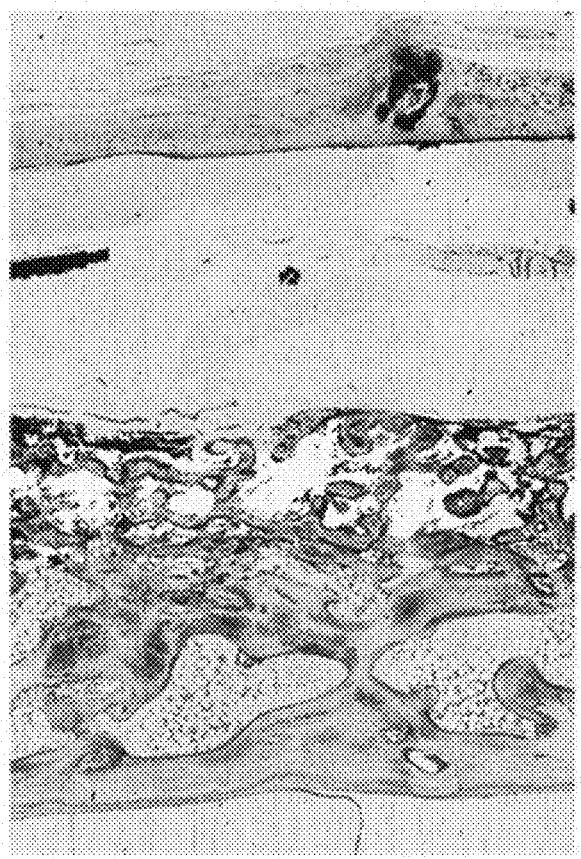
FIG. 19B shows an expanded view of the boxed region in FIG. 19A.

An angle between the right and left calvarial bones of a rabbit was measured and found to be 150° (FIG. 16). A circle with a radius, r, of 5 mm was drawn with its center coinciding with the point of intersection of the two calvarial bones. The segment enclosed by the major arc (represented by a bold curve in FIG. 17) and the two radii represents a cross section of the newly created space. The angle, α, is 150°.

The arc length, L, was calculated from the equation:

$$2\pi r - \frac{150 \times 2\pi r}{360} = 18.33 \text{ mm}$$

Thus a length of the at least one strip used in the membrane for Example 2 was about 18 mm.

Example 2 Experimental Results

There were 12 rabbits in the experimental group and a membrane was placed on the calvarial bones. There were 6 rabbits in the control group and a membrane with the layers only (i.e. without the strip) was placed on calvarial bones. Each group was further divided into two subgroups according to sacrifice time (2 and 4 months).

Figure 20:
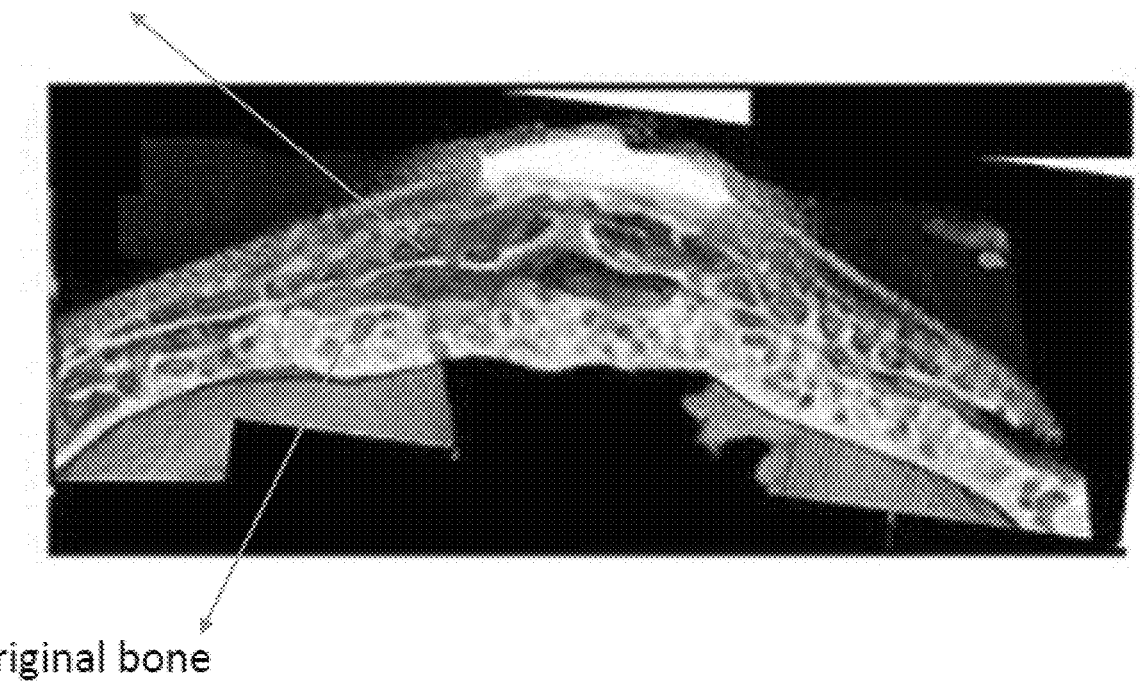
FIG. 20 is a micro CT image of the calvarial of the rabbit in the experimental group in which the membrane was left in the rabbit for 4 months.
Figure 21:
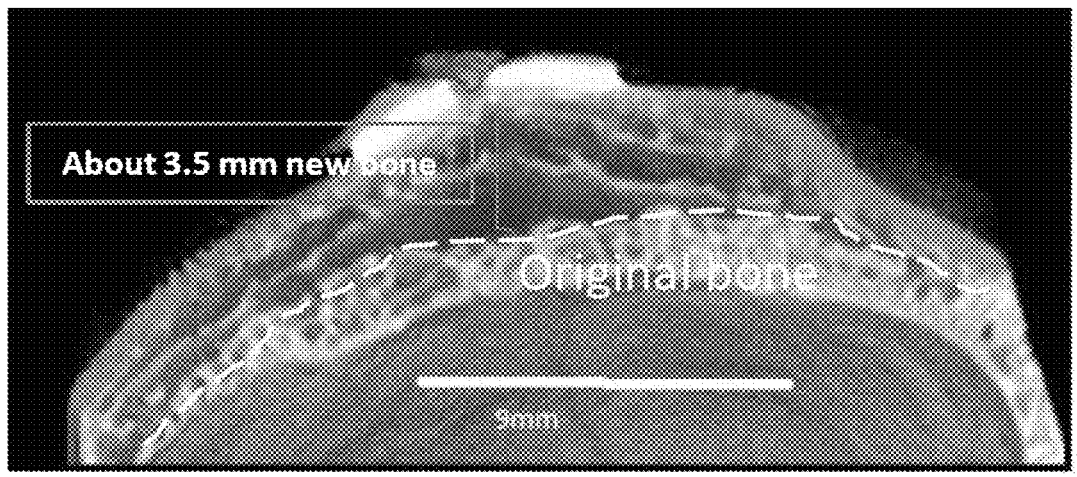
FIG. 21 is another micro CT image of the calvarial of the rabbit in the experimental group in which the membrane was left in the rabbit for 4 months.
Figure 22:
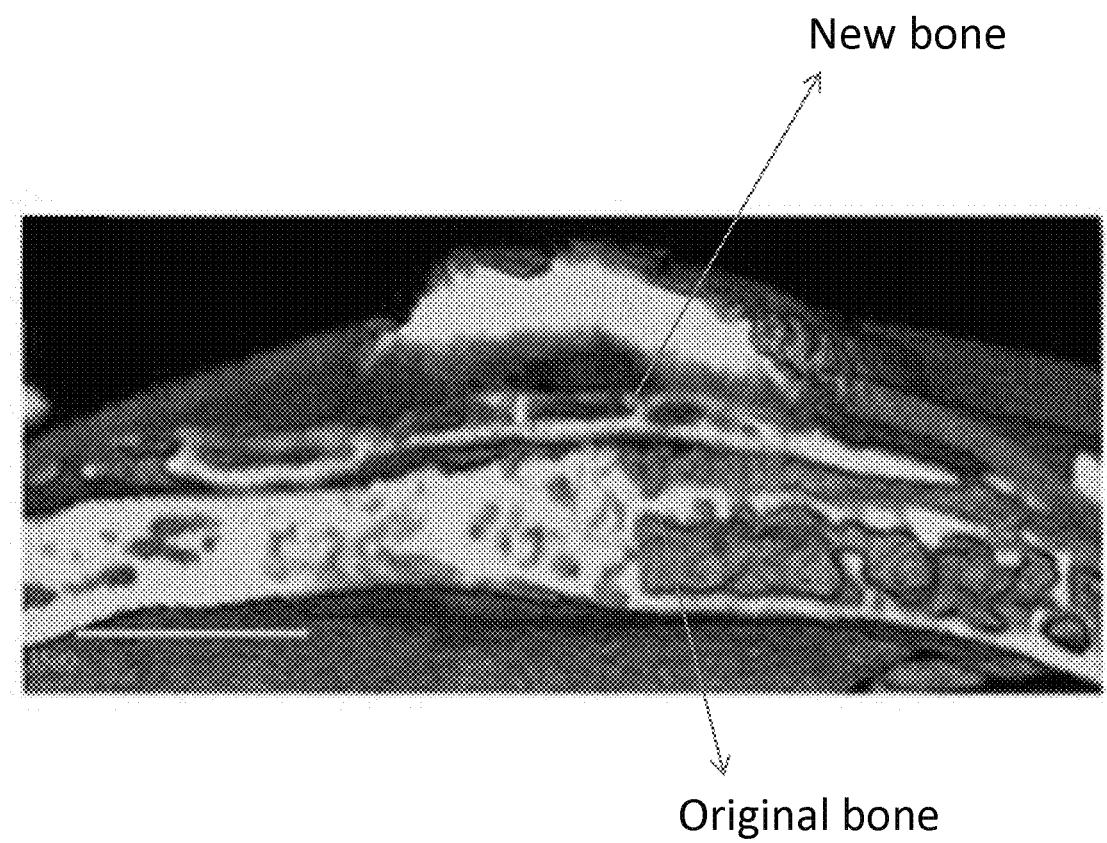
FIG. 22 is a micro CT image of the calvarial of the rabbit in the experimental group in which the membrane was left in the rabbit for 2 months.

FIGS. 18A, 18B, 19A, and 19B are histological images showing new bone has formed on top of the original bone. FIGS. 20-22 are micro CT images showing new bone has formed on top of the original bone. FIG. 21 shows about 3.5 mm of new bone has formed.

In the experimental group, the original bone thickness was increased by 1.8±0.49 mm by the end of 4 months and 1.5±0.23 mm by the end of 2 months. In the control group, the original bone thickness increased about 0.5 mm regardless of the sacrifice time.

In summary, the membrane has fulfilled the following requirements in regenerating bone:

1. Wound stability for inducing blood clot formation;
2. Primary closure of the wound for undisturbed and uninterrupted healing;
3. Facilitated angiogenesis which provided the necessary blood and undifferentiated mesenchymal cells;
4. Created and maintained a space for bone regeneration; and 5. Isolated the created space from non-osteogenic soft tissues.

The invention claimed is:

1. A membrane for guided bone regeneration, comprising:
   a first layer comprising silicone and a second layer comprising silicone, wherein each layer is one continuous sheet of silicone; and
   at least one strip comprising a shape memory material comprising nickel and titanium, wherein the at least one strip is sandwiched between the first layer and the second layer, wherein the at least one strip is one continuous strip of the shape memory material;
   wherein each of a breadth and a length of the first layer and the second layer is independently in a range of 10-60 mm, a thickness of the first layer and the second layer is independently in a range of 0.01-1 mm, a width of the at least one strip is in a range of 2-10 mm, a length of the at least one strip is in a range of 7-30 mm, a thickness of the at least one strip is in a range of 0.05-1 mm, the at least one strip is flat at a temperature in a range of 10-30° C. and is in a shape of a curve at a temperature greater than 30° C. and less than 40° C., and
   wherein the membrane does not contain voids.

2. The membrane of claim 1, wherein the length of the at least one strip is in a range of 10-20 mm and the width of the at least one strip is in a range of 3-7 mm,
   wherein a mid-point of the at least one strip coincides with a mid-point of the first layer and a mid-point of the second layer, and
   wherein the first layer and the second layer are in a shape of a rectangle, the length of the first and the second layers is in a range of 20-30 mm, and the breadth is in a range of 10-15 mm.

3. The membrane of claim 2, wherein a single strip is present and the length of the single strip is disposed parallel to the length of the first layer and the second layer.

4. The membrane of claim 1, wherein the at least one strip is irreversibly attached to a top surface of the first layer and a bottom surface of the second layer.

5. The membrane of claim 1, wherein the first layer and the second layer are in a shape of a square with the length and the breadth being the same and in a range of 20-30 mm, and
   wherein a mid-point of the at least one strip coincides with a mid-point of the first layer and a mid-point of the second layer.

6. The membrane of claim 5, wherein two strips are present, a mid-point of a first strip overlaps with a mid-point of a second strip, and the two strips are disposed perpendicularly with respect to each other.

7. The membrane of claim 6, wherein the two strips have a same length and a same breadth.

8. The membrane of claim 1, wherein the curve is an arc and a length of a chord of the arc is in a range of 40-70% of the length of the at least one strip.

9. The membrane of claim 8, wherein a length of a sagitta of the arc is in a range of 10-30% of the length of the at least one strip.

* * * * *